United States Patent [19]

Zimmerman et al.

[11] Patent Number: 5,101,016

[45] Date of Patent: * Mar. 31, 1992

[54] FACTOR VIII COAGULANT POLYPEPTIDES AND MONOCLONAL ANTIBODIES TO THEM

[75] Inventors: Theodore S. Zimmerman; Carol A. Fulcher, both of La Jolla, Calif.

[73] Assignee: Scripps Clinic and Research Foundation

[*] Notice: The portion of the term of this patent subsequent to Aug. 15, 2006 has been disclaimed.

[21] Appl. No.: 595,148

[22] Filed: Oct. 10, 1990

Related U.S. Application Data

[63] Continuation of Ser. No. 387,021, Jul. 28, 1989, abandoned, which is a continuation of Ser. No. 778,297, Sep. 20, 1985, Pat. No. 4,857,635, which is a continuation of Ser. No. 556,508, Nov. 30, 1983, abandoned, which is a continuation-in-part of Ser. No. 481,105, Mar. 31, 1983, abandoned.

[51] Int. Cl.$^5$ .............................................. A61K 37/02
[52] U.S. Cl. .................................... 530/383; 530/829; 530/407; 514/2; 514/21; 514/834; 424/529; 210/632
[58] Field of Search ............... 530/383, 419, 407, 829; 210/632; 424/529; 514/2, 21, 834

[56] References Cited

PUBLICATIONS

Burke et al., JBC. 261, #27, 12574, 1986.

*Primary Examiner*—Thurman K. Page
*Assistant Examiner*—G. S. Kishore
*Attorney, Agent, or Firm*—Morgan & Finnegan

[57] ABSTRACT

Polypeptides have been discovered which exhibit high specific VIII:C coagulant activity. Monoclonal antibodies to the polypeptides are also disclosed.

10 Claims, No Drawings

FACTOR VIII COAGULANT POLYPEPTIDES AND MONOCLONAL ANTIBODIES TO THEM

This is a continuation of co-pending application Ser. No. 07/387,021 filed July 28, 1989 now abandoned which is a continuation of Ser. No. 778,297 filed Sept. 20, 1985 now U.S. Pat. No. 4,857,635, issued 6-10-89 which is a continuation of Ser. No. 556,508 filed Nov. 30, 1983 which is a continuation-in-part of Ser. No. 481,105, now abandoned filed 3/31/83 now abandoned.

BACKGROUND OF THE INVENTION

This invention relates to new factor VIII polypeptides, that is, proteins, exhibiting coagulant activity. The invention therefore has utility in the therapy for classic hemophilia, and in the further study and characterization of the polypeptide or polypeptide complexes which provide desired clotting behavior to the blood of humans and other mammals.

It has long been known that plasma factor VIII plays a crucial role in blood coagulation, and that thrombin activates the coagulant effect of factor VIII. Recent attempts to characterize factor VIII have postulated that factor VIII is a complex of at least two polypeptides, which are known as VIII:C and VIII:R, and have found coagulant activity to reside in the VIII:C portion. Studies of the effect of thrombin on factor VIII:C have led to the conclusion that thrombin activates this factor by breaking it down into several smaller polypeptides. However, no prior studies have been able to associate thrombin-induced factor VIII activation in humans with any defined polypeptides formed from human factor VIII:C.

For instance, Hoyer and Trabold, in "The effect of thrombin on human factor VIII", J. Lab. Clin. Med. 97:50–64 (1981), sought to purify human factor VIII:C by immunoadsorbent chromatography using a polyclonal antibody to factor VIII:R raised in the rabbit. They then incubated the factor VIII:C with purified human α-thrombin, and determined that small amounts of the thrombin activated the factor VIII:C whereas larger amounts activated it less or not at all. They also concluded that thrombin activation is accompanied by a decrease in the size of the protein, and they proposed a molecular weight of about 116,000 for the activated factor VIII:C. Most significantly, they could not identify specific polypeptides that retained factor VIII:C activity and VIII:C antigen determinants.

Fulcher, C. A. and Zimmerman, T. S. in "Characterization of the human factor VIII procoagulant protein with a heterologous precipitating antibody", Proc. Natl. Acad. of Sci. USA, 79:1648–1652 (1982) obtained highly purified human factor VIII:C from plasma concentrate by passing the concentrate through a column containing a monoclonal antibody to factor VIII:R, eluting the VIII:C from the adsorbed VIII:C/VIII:R complex, and concentrating the factor VIII:C on a second column. The purified factor VIII:C was then analyzed by sodium dodecyl sulfate/polyacrylamide gel electrophoresis (hereafter, "SDS-PAGE"), both before and after addition of thrombin to the purified material. The purified factor VIII:C prior to thrombin addition showed a wide array of bands on SDS-PAGE corresponding to polypeptides of various molecular weights ($M_r$), including a relatively strong doublet at $M_r$ of 80,000 and 79,000, and at least six additional faintly staining polypeptides with larger $M_r$ including one at $M_r$ about 92,000. Addition of thrombin to the purified factor VIII:C caused the diminution or disappearance of all of the polypeptides shown prior to thrombin addition.

The coagulant activity of the plasma concentrate rose following thrombin addition to a maximum of three times that of the material prior to thrombin addition, and then diminished. The coagulant activity of the purified factor VIII:C also rose to a maximum of three times that of the pre-activated material. That is, the thrombin had essentially the same activating effect on the factor VIII:C in each case. Thus, whereas the purified factor VIII:C possessed a reported specific activity some 3280 times that of the starting material, one skilled in this art would conclude that the increase in specific activity was due to the high degree of purification achieved. There is no basis in this article for ascribing activated coagulant activity to any specific one or more of the large number of polypeptides associated with the bands observed in the purified factor VIII:C prior to activation with thrombin.

SUMMARY OF THE INVENTION

One aspect of the present invention is a factor VIII:C coagulant polypeptide complex characterized in that:
(i) the complex has one or more polypeptides which exhibit a band at a point corresponding to an $M_r$ of about 92,000; or bands at points corresponding to $M_r$ values of about 92,000 about 80,000, and about 79,000; or of about 92,000, about 72,000 and about 71,000; or of about 92,000, about 80,000, about 79,000, about 72,000, and about 71,000; when subjected to sodium dodecyl sulfate-polyacrylamide gel electrophoresis in accordance with Procedure A described in the Example hereinbelow;
(ii) the complex exhibits specific coagulant activity higher than 1800 Units/mg, and preferably higher than 5400 Units/mg;
(iii) the complex exhibits the activity in step (ii) over a continuous period of at least about 10 minutes; and
(iv) the complex binds to an antibody for human factor VIII:C.

Other aspects of the invention include biological preparations containing the complex, and the treatment of the clotting disorders of hemophilia by administering the complex or preparations thereof. Yet another aspect of the present invention comprises making the complex, or a concentrated preparation thereof, by digesting human factor VIII:C with α-thrombin, discontinuing the digestion while the complex described above is present, and concentrating the complex. A further aspect of the invention is a process for recovering VIII C polypeptides, without losing coagulant activity, from an immunoadsorbent containing monoclonal antibodies to factor VIII:C.

DETAILED DESCRIPTION OF THE INVENTION

As indicated, the present invention encompasses polypeptide complexes which exhibit factor VIII:C coagulant activity and factor VIII:C immunological behavior, and which show characteristic $M_r$ value(s) when analyzed by sodium dodecyl sulfate-polyacrylamide gel electrophoresis (hereafter, "SDS-PAGE"). By "polypeptide complex" is meant not only distinct, but also preparations containing only one discernible polypeptide, i.e., that which exhibits a band at an $M_r$ of 92,000.

The description below showing the preparation of the claimed complex utilizes human factor VIII:C which has been highly purified, in order to free the identification and characterization of the novel product from the effects of extraneous polypeptides. It should be recognized, though, that the invention itself is not dependent on how the starting material has previously been treated, except where specifically indicated. The active factor VIII:C polypeptides of the present invention can be prepared not only by digestion with thrombin as described in greater detail below, or with other similarly acting proteases such as Factor Xa, Factor IXa, or Russell's viper venom-V, but also by recombinant DNA techniques in which the polypeptides of interest are produced by bacteria, yeast, or other cells into which one or more genes for producing the polypeptides of interest are inserted by techniques known to those of ordinary skill in the art. Either process for producing the complex of interest can be expected to produce the complex in a mixture with one or more other polypeptides.

Any plasma or plasma concentrate containing human factor VIII:C can be employed to advantage. The novel coagulant polypeptide complex can be prepared from human factor VIII:C which has been ultrapurified in accordance with the process described in U.S. Pat. No. 4,361,509, issued Nov. 30, 1982, the disclosure of which is hereby incorporated herein by reference. In that process, a source of factor VIII:C such as plasma or a plasma concentrate is passed through an immunoadsorbent column to which monoclonal antibodies to factor VIII:R have been attached. The factor VIII:R-/VIII:C complex is adsorbed on the column, and then the factor VIII:C is eluted and passed through a second column such as aminohexyl agarose. It should be noted that the second column can also be an immunoadsorbent containing antibodies to factor VIII:C. The factor VIII:C should be kept free of $\alpha$-thrombin and other proteases. The factor VIII:C is conveniently stored in a saline, buffered solution containing, e.g., 0.3M calcium chloride, at a pH of about 6.8 to about 7.4.

The human factor VIII:C is then digested with $\alpha$-thrombin under conditions effective to form the polypeptide complex described below. The purified $\alpha$-thrombin can be prepared by the procedure described by Fenton, J. W. II; Fasco, M. J.; Stackrow, A. B.; Aronson, D. L.; Young, A. M.; and Finlayson, J. S. "Human Thrombin. Production, Evaluation, and Properties of $\alpha$-Thrombin". J. Biol. Chem. 252: 3587-3598 (1977).

The $\alpha$-thrombin and the factor VIII:C are combined in an aqueous system, preferably buffered at a pH of about 6.8 to about 7.4. The thrombin should be present in an amount relative to the factor VIII:C that is sufficient to permit reaction with the factor VIII:C, but not so high that the factor VIII:C degrades to inactive polypeptides before the desired active polypeptide complex can be recovered. As an illustration, a preparation containing 200-400 units (0.2 mg/ml) of factor VIII:C per ml should be digested with about 0.1 to about 0.5 units/ml of $\alpha$-thrombin. The digestion can proceed at room temperature; too high a temperature can denature the polypeptides, and too low a temperature can retard the progress of the digestion.

The digestion is allowed to proceed for a time long enough to permit the formation of the desired polypeptide complex. The optimum time will be from 0.1 to about 60 minutes, with times from 0.1 to 30 minutes preferred. Times from 1 to 10 minutes have been found highly satisfactory, although it will be recognized that optimum times can be identified with minimal experimentation using aliquots of the factor VIII:C starting material being treated. An optimum time is that which forms the maximal amount of the polypeptide complex exhibiting an $M_r$ of about 92,000, accompanied by the formation of a protein complex exhibiting an $M_r$ doublet of about 79,000 and about 80,000, without degrading the $M_r$ 92,000 polypeptide significantly. The $M_r$ 79,000-80,000 doublet may possibly function after it has undergone degradation to a complex exhibiting a doublet at $M_r$ values of 71,000-72,000. The 71,000-72,000 doublet alone does not exhibit factor VIII:C activity.

The digestion is then discontinued by adding to the reaction mixture an effective amount of (p-amidinophenyl) methanesulfonyl fluoride (hereafter, "p-APMSF") or another thrombin inhibitor. The p-APMSF prevents the $\alpha$-thrombin from reacting further with the factor VIII:C proteins, without itself degrading those proteins. The amount of p-APMSF to add should comprise about 1.5 to about 2.5 millimoles per unit of $\alpha$-thrombin activity initially present in the reaction mixture.

p-APMSF can be obtained through California Medicinal Chemistry Company, San Francisco, Calif., and its preparation is described in Laura, R.; Robinson, D. J.; and Bing, D. H. "(p-Amidinophenyl)methanesulfonyl Fluoride, an Irreversible Inhibitor of Serine Proteases", Biochemistry (1980) 19, 4859-4864, at 4861.

The reaction mixture can then be treated to concentrate the polypeptide complex comprising the present invention. Preferably, the polypeptide complex is concentrated with respect to other factor VIII and non-factor VIII proteinaceous material, to provide the complex in a form which affords the very high activity possessed by the complex in the purified form. Purification techniques include, for example, ultrafiltration, ultracentrifugation, ion exchange, gel permeation chromatography, preparative electrophoresis, isoelectric focusing, and gel and affinity chromatography.

The desired complex can also be concentrated and/or recovered by passing the reaction mixture, which can already have been concentrated by another technique, through an immunoadsorbent column containing anti-human VIII:C antibodies, or equivalent antibodies against VIII:C other than human, that react with the polypeptides(s) of the complex. The antibodies are attached to agarose (see Example I below). Several antibodies which can be used to concentrate the complex and/or isolate certain of the polypeptides thereof are described below. The active VIII:C complex adsorbs preferentially to the column, and is then eluted from the column with a solution of calcium ions (e.g., $CaCl_2$) which can optionally also contain a non-ionic surfactant. Suitable non-ionic surfactants include alkyl phenyl polyoxyethylenes such as Triton-X-100, -N-101, or -X-405 (Eastman Chemical Co.); Tween-20, -60 or -80 (Sigma Chemical Co.); and Nonidet P-40 (Sigma Chemical Co.); all of these well-known articles of commerce having known chemical formulas.

The amounts of calcium ion and surfactant to use should be high enough to desorb the polypeptide complex, but not so high that the eluant inactivates the polypeptide. A calcium ion concentration of up to about 0.5M or even up to 1.0M is satisfactory, and 0.25M is preferred. A surfactant concentration of up to about 1 wt. % is satisfactory, and about 0.1 wt. % is preferred.

The eluant is applied to the immunoadsorbent column at about 1 to about 8 bed volumes per hour, and preferably about 3 to about 4 per hour. Too high a flow rate risks disruption of the column and non-absorption of the polypeptide complex. The skilled practitioner will readily adapt these guidelines to immunoadsorbent processes other than fixed-bed columns.

The VIII:C polypeptide complex is recovered in a suitable buffer, at a pH of about 6.8 to 7.4, which also contains calcium ion and surfactant from the eluant solution. The calcium and surfactant concentrations can be lowered, and the surfactant preferably removed, such as by dialyzing the solution against a buffer such as the VIII:C buffer used in Example 1 which contains a lower amount of calcium ion. The complex of this invention can be stored in this solution, or lyophilized. The complex can be administered to patients with hemophilic clotting disorders by adjusting the calcium content to be physiologically compatible and injecting a steril saline solution thereof.

When analyzed by SDS-PAGE as shown below, the complex of this invention exhibits an $M_r$ of about 92,000, and can normally contain material exhibiting an $M_r$ doublet of about 79,000 and about 80,000, some of which can have undergone degradation to exhibit an $M_r$ doublet of about 71,000 and about 72,000. In its purified form, this band or the group of these bands are essentially the only bands that appear. However, it will be appreciated that the present invention also encompasses biological preparations in which less than 100%, i.e., 95%, 90%, or even 80%, 70% or 60%, or even as little as 30%, 20%, 10%, or 1% of the proteinaceous matter present comprises the complex of the present invention. The invention thus encompasses preparations in which the factor VIII:C activity is due to the presence of the complex.

The protein complex of the present invention possesses specific VIII:C coagulant activity (that is, activity per milligram of all protein present) higher than that exhibited by purified human factor VIII:C, for instance human factor VIII:C purified by the process disclosed and claimed in the aforementioned U.S. Pat. No. 4,361,509. Indeed, the activity of the purified complex should be several times, e.g., 3 to 5 times, that of purified human factor VIII:C, and is advantageously at least 10 times or even 50 times as active. Likewise, biological preparations comprising the complex of this invention in association with one or more other proteins can be prepared which exhibit higher specific activity than that afforded in previously known coagulant preparations. The specific activity of the complex, and of biological preparations containing it, is higher than 1800 Units/mg, advantageously higher than 5400 Units/mg, and in more advantageous embodiments exceeds 7,500 and even 10,000 Units/mg. Preferably, the specific activity of the inventive preparations exceeds that of the purified human factor VIII:C used herein by a factor of 3 to 5, and more advantageously by at least 10 times, by 50, or even by 100 times.

The protein complex of the present invention, and biological preparations thereof, are characterized in that the enhanced activity described above remains present over a continuous period of at least about 10 minutes and preferably at least about 30 minutes. Of course, activity will generally be stable for much longer. The complex also possesses the immunological characteristics of a factor VIII:C protein, i.e., it binds to an antibody for human factor VIII:C. This can be ascertained, for instance, by growing a monoclonal antibody to factor VIII:C as described below, attaching the antibody to an agarose column, passing an aqueous solution of the complex through the column, and assaying the resultant solution for factor VIII:C activity.

A further desirable attribute of this invention is that the polypeptides of $M_r = 92,000$ and $M_r = 79,000-80,000$ are stable, relative to native human factor VIII:C which is notoriously susceptible to proteolysis, degradation, and resultant loss of coagulant activity. This stability is demonstrated by the polypeptides' ability to survive the treatment steps described herein.

EXAMPLE I

This Example shows how factor VIII:C was purified from commercial concentrate and digested with purified α-thrombin. A monoclonal antibody to factor VIII:C was produced and used to identify VIII:C polypeptides. At several selected points during the digestion, portions of the digestion mixture were assayed for VIII:C (coagulant) activity, and for protein bands using SDS-PAGE.

Purification of VIII:C. All steps were at room temperature Chemicals were reagent grade. 40 bottles of commercial factor VIII concentrate (provided by Armour Pharmaceutical) were reconstituted in 1000 ml of VIII:C buffer (0.02M imidazole/0.15M sodium chloride/0.1M L-lysine HCl/0.02% sodium azide, pH 6.8). This sample, which contained a total of 17,000 units of VIII:C activity, was applied to a 2.5-3.0 liter bed volume immunoadsorbent column. The column was cyanogen bromide-activated agarose (Sepharose 4B, Pharmacia, Piscataway, N.J.), to which monoclonal antibodies to VIII:R had been covalently bonded. The antibodies were raised and attached to the column as described in the aforementioned U.S. Pat. No. 4,361,509. The antibodies were precipitated from ascites fluid using 50% ammonium sulfate, reprecipitated two more times, and then attached to the column at a density of 2-4 mg/ml of Sepharose. The immunoadsorbent was pre-eluted with 3M sodium thiocyanate, washed with VIII:C buffer (0.02M imidazole HCl pH 7.0, 0.15M NaCl, 0.1M L-lysine-HCl, 0.02% sodium azide), treated twice with 2 mM di-isopropyl fluorophosphate, and then the concentrate was added.

The column was washed with 20 liters of VIII:C buffer containing 0.15M sodium chloride, and VIII:C was then eluted from the VIII:R with VIII:C buffer containing 0.35M calcium chloride. Active fractions were pooled and concentrated under nitrogen pressure 100-fold in an Amicon stirred cell with a YM10 membrane. The concentrate was then diluted 1:10 in VIII:C buffer and applied to a 4 ml column of aminohexyl-Sepharose (Pharmacia) equilibrated in VIII:C buffer containing 0.025M calcium chloride, VIII:C was eluted in high concentration with VIII:C buffer containing 0.3M calcium chloride at a flow rate of 10 ml/hr. The concentrated immunoadsorbent pool was adjusted to 0.25M calcium chloride and adsorbed twice for 1 h each time with 1/10 vol/vol of a mixture of monoclonal anti-fibrinogen, anti-fibronectin and anti-vWF antibodies which had been coupled to cyanogen bromide-activated Sepharose.

Production of monoclonal antibody again VIII:C. Monoclonal antibodies were produced as described in U.S. Pat. No. 4,361,509 using purified VIII:C as immunogen. The antibodies were selected with a solid-phase assay in Linbro-Titertek (Flow Laboratories, Inglewood, Calif.) plates and an enzyme-linked immunoadsorbent (ELISA) detection system described in Engvall, E. and Perlmann, P. "Enzyme-linked immunoadsorbent assay (ELISA), Quantitative assay of immunoglobulin G" Immunochemistry 8:871-874 (1971)) using a peroxidase-antibody conjugate (Zymed Laboratories, Burlingame, Calif.). The plates were coated with 100 ng of purified VIII:C per well. The ELISA-positive culture supernatant of the clone selected for use in this study also inhibited plasma VIII:C activity.

Thrombin activation time course analysis of purified VIII:C. Purified human α-thrombin(sp. act. 2534 U/mg, final concentration 0.5 U/ml), was added to the purified VIII:C (final concentration 167 ug/ml) in imidazole saline buffer containing 0.04M $CaCl_2$. Buffer alone was added to a control aliquot. The solutions were incubated at room temperature and at various time intervals samples of the VIII-C-thrombin mixture were added to tubes containing p-APMSF (California Medicinal Chemistry Co.) to inactivate the thrombin rapidly and irreversibly. In order to minimize hydrolysis of p-APMSF, it was diluted 1:10 from a stock solution (100 mM in methanol) into imidazole saline buffer 60 seconds before reaction with the VIII:C-thrombin samples. The final p-APMSF concentration was 1 mM. The control aliquot was treated similarly with p-APMSF at the start of the experiment. At the end of the 60 minute time course, all VIII-C samples were assayed for VIII:C acitivity using an activated partial thromboplastin time assay described in the literature and then prepared for SDS-PAGE.

SDS-PAGE "Procedure A":

Discontinuous SDS polyacrylamide slab gel electrophoresis was performed based on the procedure of Laemmli, U. K., Nature 227, 680–685, 1970. The "Procedure A" followed is:

I. Sample Preparation
1 Dialyze the protein sample (ideally 50–100 microliters containing 5–60 micrograms of protein) against sample buffer overnight at room temperature. If the sample contains calcium ion, include 10 millimolar ethylenediamine tetracetic acid (EDTA) in the sample buffer.
2. Place the dialyzed sample in a tube and add 1/10 volume of 10% SDS. Cover the tube with aluminum foil. Heat the sample in a boiling waterbath for 10 minutes.
3. Remove the sample from the waterbath and add to it 1/10 volume of 500 millimolar dithiothreitol. Incubate it at 56° C. for 4 hours.
4. Allow the sample to cool to room temperature and prepare it for layering onto the gel by adding stock glycerol solution to 10% final concentration and stock bromophenol blue dye solution to 0.05% final concentration.

11. Preparation of gel solutions (use deionized, distilled water)
1. Stock glycerol solution: 50% glycerol
2. Stock bromophenol blue dye solution: 0.5% bromophenol blue
3. Lower gel stock solution: 18.2 grams of Tris base 4 ml of 10% SDS final volume 100 ml. Ajust pH to 8 8 with concentrated hydrochloric acid. Filter.
4. Upper gel stock solution: 6.1 grams of Tris base 4 ml of 10% SDS Final volume 100 ml Adjust pH to 6.8 with concentrated hydrochloric acid. Filter.
5. Sample buffer 0.01M sodium phosphate 1.0% SDS 10 millimolar disodium EDTA Final volume 1 liter pH adjusted to 7.0 with sodium hydroxide or phosphoric acid.
6. Acrylamide stock solution: Dissolve 30 g of acrylamide in 50 ml of water and add 0.8 g of bisacrylamide and dissolve. Bring to 100 ml final volume. Filter the solution and store in the dark at 4° C.
7. Stock electrode buffer solution: 30.3 g Tris base 144.1 g glycine final volume 1 liter
8. Electrode buffer 100 ml of stock electrode buffer solution 890 ml water 10 ml of 10% SDS
9. Stock Coomassie blue dye solution 1% Coomassie blue R 250 in water Dissolve with stirring for at least 30 minutes at room temperature and filter.
10. Ammonium persulfate solution 10% ammonium persulfate. Stored in dark at 4° C. and made fresh every week.

III. Gel Preparation and Running: Final acrylamide concentration=7.5%

Lower gel solution

| 20 ml of lower gel | |
|---|---|
| Stock lower gel solution | 5 ml |
| Stock acrylamide solution | 5 ml |
| Water | 10 ml |
| N,N,N',N'-tetramethylethylenediamine (TEMED) | .005 ml |
| 10% ammonium persulfate | 0.1 ml |

2. Upper gel solution

| 10 ml of upper gel | |
|---|---|
| Stock upper gel solution | 2.5 ml |
| Stock acrylamide solution | 1.0 ml |
| Water | 6.5 ml |
| N,N,N',N'-tetramethylethylenediamine (TEMED) | 0.01 ml |
| 10% ammonium persulfate | 0.03 ml |

3. Procedure
   a. Prepare the slab gel apparatus for a 14.5 cm×9.0 cm×0.8 mm slab gel. The apparatus is a standard gel electrophoresis apparatus, available, for instance, from Hoeffer Scientific Instruments, San Francisco, Calif.
   b. Mix all lower gel ingredients except the TEMED and ammonium persulfate in a 50 ml vacuum flask and de-aerate. Then add the TEMED and ammonium persulfate, mix gently and pour the lower gel immediately. Layer the lower gel with water-saturated butanol and allow it to polymerize undisturbed for at least 1 hour, preferably 2–6 hours.
   c. Pour off the butanol layer and rinse the top of the lower gel with the complete upper gel mixture. (The upper gel mixture is prepared, de-aerated and TEMED and ammonium persulfate are added as for the lower gel above).
   d. Pour the upper gel and insert the comb into the upper gel allowing at least 1.0 cm between the bottom of the comb teeth and the upper gel-lower gel interface. Fill with upper gel solution as full as possible. Allow upper gel to polymerize at least 1 hour before running the gel.
   e. To remove the comb, pipet electrode buffer over the top of the upper gel and gently remove the comb. Rinse the upper gel wells with electrode buffer several times.

f. Assemble the apparatus for running and add electrode buffer. Apply the sample(s) by layering it into the upper gel wells underneath the buffer layer.

g. Run the gel using constant current: 8 milliamperes while samples are in the upper gel and 15 milliamperes while samples are in the lower gel. Stop the electrophoresis when the bromophenol blue dye front is 1.0 cm from the bottom of the lower gel.

IV. Fixing and Staining the gel

Reference: Fairbanks, G., Steck, T. L., and Wallach, D. F. N., Biochemistry 10, 2606–2617, 1971.

1. Fix the gel at least overnight in a sealed chamber in a solution containing 25% isopropanol, 10% acetic acid, 10 ml of 1% Coomassie blue stock solution, final volume 400 ml.
2. Next, soak the gel at least 1 hour in 10% isopropanol, 10% acetic acid and 1.0 ml of 1% Coomassie blue stock solution, final volume 400 ml.
3. Soak the gel about 4 hours in 10% acetic acid with changes or until completely destained.
4. The destained gel can be dried onto filter paper using a gel fryer to increase contrast.

Approximately 5–20 g of protein was applied to the gels. VIII:C $M_r$s were calculated for reduced samples by semilogarithmic plots of $M_r$ versus migration distance, using reduced fibronectin ($M_r$ 200,000), phosphorylase b ($M_r$ 95,000), bovine serum albumin ($M_r$ 68,000), and IgG heavy chain ($M_r$ 50,000), and ovalbumin ($M_r$ 43,000) as standards.

Scanning and integration of a photographic print of the finished gel was done using a Zeineh soft laser scanning densitometer.

Results. The specific activity of the purified factor VIII:C was 2000 units/mg. Thrombin activation of purified VIII:C activity was analyzed over a 60 minute time course. Before thrombin exposure the untreated VIII:C sample showed the characteristic array of VIII:C forms ranging from a doublet at $M_r$=79,000–80,000 to a band at $M_r$=188,000. A band above $M_r$=188,000 and two bands below $M_r$=79,000 did not bind to the monoclonal anti-VIII:C antibody immunoadsorbent. The bands between $M_r$=79,000 and $M_r$=188,000 did bind to the anti-VIII:C antibody.

During the first 5 minutes of the thrombin activation time course, all but one of the monoclonal anti-VIII:C antibody reactive bands with an $M_r$ greater than 92,000 gradually disappeared and were undetectable when VIII:C activity reached its peak at 5 minutes.

A band at $M_r$=122,000 appeared thrombin-resistant in only some experiments, but after extensive thrombin treatment neither this band nor any other band was reactive with the immobilized monoclonal anti-VIII:C antibody.

A band at $M_r$=92,000 increased in intensity as VIII:C activity increased. A doublet at $M_r$=79,000 and 80,000 appeared to be converted to a doublet at $M_r$=71,000–72,000, with the latter form predominant from 5 to 60 min. as VIII:C activity decreased. Two bands, at $M_r$=54,000 and $M_r$=44,000, became clearly visible from 5 to 60 min. The $M_r$=44,000 band also appeared as a doublet in some experiments. The $M_r$=71,000–72,000 doublet, the $M_r$=54,000 band and the $M_r$=44,000 band were not removed to a significant degree by the immobilized monoclonal anti-VIII:C antibody.

Scanning and integration of the gel discussed above allowed correlation of changes in polypeptide concentration with changes in VIII:C activity. The results are shown in the Table. As shown, the $M_r$=92,000 band increased and then decreased in concentration in parallel with VIII:C activity. This suggests that the $M_r$=92,000 band is an active form of VIII:C whose concentration increased with thrombin activation. The $M_r$=54,000 and $M_r$=44,000 bands increased steadily in concentration between 1 and 40 min., even after activity of the mixture declined.

Most of the $M_r$=79,000–80,000 doublet was lost during the first 0.1 to 10 min. as VIII:C activity peaked, while most of the $M_r$=71,000–72,000 doublet appeared during this time and predominated even as VIII:C activity decreased. These data suggest that the $M_r$=71,000–72,000 doublet was derived from the $M_r$=79,000–80,000 doublet and that the $M_r$=71,000–72,000 doublet is inactive by itself. These data are consistent with the retention by the $M_r$=71,000–72,000 doublet of the ability to complex with the $M_r$=92,000 polypeptide; this complex would also have activity.

Direct evidence that the $M_r$=92,000 polypeptide is complexed with the $M_r$=79,000–80,000 doublet derives from experiments utilizing the anti-VIII:C monoclonal immunoadsorbent. It was first shown that the monoclonal antibody reacts predominantly with the $M_r$=79,000–80,000 doublet and not with the $M_r$=92,000 polypeptide. This was shown by electrophoretic transfer experiments. Then it was shown that the monoclonal anti-immunoadsorbent removed both the $M_r$=79,000–80,000 doublet and the $M_r$=92,000 polypeptide from the solution. The $M_r$=92,000 polypeptide could be eluted from the anti-VIII:C immunoadsorbent column with 10 mM EDTA, whereas the $M_r$=79,000–80,000 doublet remained bound. The doublet could be subsequently eluted with 3M sodium thiocyanate. These experiments demonstrated that the $M_r$=92,000 polypeptide bound to the immunoadsorbent because it was complexed with the $M_r$=79,000–80,000 doublet and that it was this doublet which bound directly to the immunoadsorbent.

| Time (min) from addition of thrombin to addition of p-APMSF: | 0* | 0.1 | 1 | 2 | 5 | 10 | 20 | 30 | 40 | 60 |
|---|---|---|---|---|---|---|---|---|---|---|
| Activity of digestion mixture | 300 | 900 | 1300 | 1350 | 1400 | 1250 | 800 | 375 | 250 | 100 |
| Amount of each polypeptide ($M_r$) present, as % of total protein present: | | | | | | | | | | |
| $M_r$ = 92,000 | 7.3 | 9.5 | 11.1 | 11.5 | 11.8 | 9.6 | 7.3 | 6.7 | 4.0 | 4.4 |
| $M_r$ = 79–80,000 | 21.9 | 18.8 | 16.1 | 12.9 | 11.0 | 8.4 | 9.0 | 8.6 | 7.4 | 7.4 |
| $M_r$ = 71–72,000 | 0.0 | 9.0 | 11.2 | 12.9 | 16.5 | 15.9 | 15.7 | 18.8 | 18.2 | 20.4 |
| $M_r$ = 54,000 | 4.9 | 5.9 | 5.1 | 5.7 | 7.1 | 9.4 | 10.2 | 11.8 | 13.7 | 13.5 |

| | | | | | | | | | |
|---|---|---|---|---|---|---|---|---|---|
| $M_r = 44,000$ | 0.0 | 0.0 | 0.0 | 3.1 | 3.7 | 5.9 | 6.1 | 7.2 | 7.8 | 7.6 |

*Measurements just prior to addition of -thrombin
Activity is in Factor VIII:C units/ml

EXAMPLE II

This Example describes the results of treating purified human Factor VIII:C with purified human activated protein C (hereafter, "APC"), a known anticoagulant enzyme. Human Factor VIII:C was purified as described above. APC was purified by the procedure described in Marlar, R. A. et al., "Mechanism of action of human activated protein C, a thrombin-dependent anticoagulant enzyme." *Blood*, Vol. 59, 1067 (1982), except that a mono S column of a Pharmacia FPLC system was used to separate APC from thrombin.

Assays: Samples were assayed for VIII:C activity as described above using an activated partial thromboplastin time assay with hemophilia A plasma substrate.

Preparation of samples for electrophoresis: Since calcium ions are required for APC activity, APC was stopped at various times by addition of 1/10 volume of 100 mM EDTA containing 10 uM DAPA to the VIII:C+APC aliquots as well as to the control VIII:C and APC aliquots. A 1/10 volume of 10% sodium dodecyl sulfate was then added to these aliquots. They were then heated in a boiling waterbath for 5 minutes and subsequently dialyzed for SDS-PAGE as described above.

Discontinuous sodium dodecyl sulfate 7.5% polyacrylamide gel electrophoresis (PAGE) of reduced VIII:C, staining with Coomassie blue R250 and scanning and integration of the gel were as described above.

Sample preparation: A 339 ug sample of VIII:C in 0.3 ml of VIII:C buffer containing 0.3M calcium chloride was dialyzed overnight against buffer (50 mM Tris-chloride, 0.15M sodium chloride, 5 mM calcium chloride, 0.02% sodium azide, pH 7.4). To the dialyzed VIII:C sample was added 1.095 ml of buffer, 90 ul of rabbit brain cephalin (Sigma Chemical Co., St. Louis, Md., reconstituted, stored and thawed according to manufacturer's instructions) and 15 ul of 1 mM dansylarginine N-(3-Ethyl-1,5-pentanediyl) amide (DAPA), to give a final DAPA concentration of 10 uM. The DAPA was included to inhibit any trace amounts of thrombin present in the APC since 10 uM DAPA does not significantly inhibit APC. The final volume of the sample was 1.5 ml and the final VIII:C concentration was 226 ug/ml. Four hundred microliters of the 1.5 ml VIII:C sample were withdrawn and set aside as a control (designated VIII:C). To the remaining 1.1 ml was added 20 ul (10 ug) of APC giving a final APC concentration of 9 ug/ml (designated VIII:C+APC). A second control sample was prepared containing all components at similar concentrations except that VIII:C was omitted (designated APC).

Timepoints: VIII:C alone, the mixture of VIII:C and APC, and APC alone were placed in a 37° C. waterbath and at given timepoints aliquots were withdrawn for SDS-PAGE and/or VIII:C activity assay. It was also determined in control that APC remained active in the hydrolysis of the synthetic substrate S-2238 after prolonged incubation at 37° C.

Results: Digestion of purified VIII:C with APC was associated with loss of approximately 85% of the control VIII:C activity. APC inactivation of VIII:C activity resulted in the diminution of all VIII:C polypeptides of $M_r$ between 92,000 and 188,000 and generation of a polypeptide of $M_r = 45,000$, while leaving the doublet of $M_r = 79-80,000$ intact.

A time course inactivation of purified VIII:C by APC showed the progressive disappearance of specific VIII:C polypeptides as VIII:C activity decreased over a 360 minute time course. Scanning and integration of the gel showed that the polypeptide $M_r = 188,000$ and the polypeptide of $M_r = 92,000$ decreased in parallel with VIII:C activity.

One other polypeptide of intermediate $M_r$ was cleaved by APC but it was not easily quantitated by gel scanning. In this experiment unlike the digestion with APC, some VIII:C polypeptides of $M_r = 92,000-188,000$ were resistant to the APC digestion. However, as in the digestion with APC, the doublet polypeptide at $M_r = 79-80,000$ was not proteolyzed by APC.

A polypeptide of $M_r = 45,000$ appeared to increase in concentration as the polypeptides of $M_r = 188,000$ and 92,000 decreased suggesting that it is a proteolytic fragment derived from them. No other digestion products were visualized with Coomassie blue.

As shown in Example 1, during thrombin activation of VIII:C the $M_r = 92,000$ polypeptide increased and decreased in parallel with VIII:C activity. In order to determine whether a linear relationship existed between proteolysis of the polypeptide of $M_r = 92,00$ and the loss of VIII:C activity, the data of this time course inactivation run were re-plotted to examine percent VIII:C activity versus percent of polypeptide of $M_r = 92,000$. The amount of VIII:C activity appeared to be proportional to the amount of the polypeptide of $M_r = 92,000$.

A further aspect of the present invention comprises monoclonal antibodies which are specific in an unforeseeable way to the various polypeptides which are formed by the reaction of factor VIII:C with a protease such as alpha-thrombin. Each antibody reacts with human factor VIII:C which has not been activated nor digested with thrombin or equivalent proteases. The antibodies are further characterized by their individual properties, as follows:

(A) One reacts with the $M_r = 92,000$ polypeptide described herein, with polypeptides of $M_r$ 108,000 and larger, and with the polypeptide of $M_r = 44,000$ which is present in terminal-thrombin digests. It does not react with the polypeptide described herein which exhibits a doublet of $M_r = 79,000-80,000$, nor with the polypeptide described herein which exhibits a doublet of $M_r = 71,000-72,000$.

(B) One reacts with the $M_r = 92,000$ polypeptide described herein, with polypeptides of $M_r = 108,000$ and larger, and with the polypeptide of $M_r = 54,000$ which is present in terminal thrombin digests. It does not react with the polypeptide described herein which exhibits a doublet of $M_r = 79,000-80,000$, nor with the polypeptide described herein which exhibits a doublet of $M_r = 71,000-72,000$.

(C) One reacts with the doublet of $M_r = 79,000-80,000$ and polypeptides of $M_r = 108,000$ and greater, but not with the polypeptide of $M_r = 92,000$, nor with the polypeptides of $M_r = 71,000-72,000$, $M_r = 54,000$, nor $M_r = 44,000$.

(D) One reacts only with polypeptides of $M_r=108,000$ and greater.

Each of these antibodies can be used to concentrate the complex described above, from mixtures which also contain other polypeptides. One such mixture is produced by partial digestion of human factor VIII:C with α-thrombin or an equivalent protease. Another such mixture is that produced by recombinant DNA techniques in which a desired polypeptide or complex is expressed by a microorganism and must be recovered from a mixture with other proteinaceous compounds. Antibody (A), (B), (C) or (D), or a combination of two, three, or all of them, can be attached to an immunoadsorbent column in the manner described in Example 1, and a feed solution of the mixture containing the polypeptide(s) comprising the complex is poured through the column. Those polypeptides having $M_r$ of 92,000, 79,000–80,000 and 71,000–72,000 which are present in the feed solution adsorb onto the column, from which they can be eluted as taught hereinabove after the source solution has been washed through the column. The resulting eluted solution is thereby concentrated in the desired activated VIII:C complex compared to the feed solution.

The new antibodies are also useful for analytical purposes, to detect the occurrence of the reaction of human VIII:C with thrombin or other proteases, because of their ability to react with products of that reaction. An antibody having profile (B) and an antibody having profile (C) have been found which neutralize VIII:C coagulant activity when either is bound to factor VIII:C. This additional property can be of value in the diagnosis of hemophilia-related disorders.

The discovery of these antibodies also permits further characterization of the components of the polypeptide complex described herein. Thus, the polypeptide which exhibits a band of $M_r=92,000$ contains (at least) two epitopes (i.e. antibody binding sites) that are not destroyed by thrombin digestion and are not present on the polypeptides which exhibit the doublet of $M_r=79,000-80,000$ nor the doublet of $M_r=71,000-72,000$. One of these epitopes is also present on the polypeptide of $M_r=44,000$, and the other on the polypeptide of $M_r=54,000$. Thus, the $M_r=54,000$ and $M_r=44,000$ polypeptides derive from the $M_r=92,000$ polypeptide. Also, the $M_r=92,000$ and $M_r=79,000-80,000$ polypeptides are derived from a common precursor or precursors. The discovery of antibodies having profile (B) and profile (C) each of which neutralizes factor VIII:C coagulant activity is further support that the $M_r=92,000$ and $M_r=79,000-80,000$ polypeptides are important to the coagulant function. The polypeptides exhibiting the doublet of $M_r=79,000-80,000$ contain an epitope which is destroyed by thrombin digestion and which is not present on the polypeptide of $M_r=92,000$.

These monoclonal antibodies can be prepared by the general steps of purification of human factor VIII:C; raising monoclonal antibodies to the purified VIII:C; partial digestion and activation of purified VIII:C to produce the polypeptide complex described above, including identification of the specific polypeptides; reaction of the anti-VIII:C antibodies with the products of the activation; and characterization of an antibody by identification of the polypeptide(s) with which it reacted. This sequence is set forth in more detail in Example III below. Alternatively, one can prepare an antibody by isolating the particular polypeptide of interest from the partial thrombin digestion products, for instance by immunoadsorbtion onto and then elution off of a column comprising agarose to which is coupled a monoclonal antibody known to react with the polypeptide of interest, and then raising a monoclonal antibody against that polypeptide using the procedure described in Example III.

EXAMPLE III

Monoclonal antibodies to human Factor VIII:C were raised using the following procedure, starting from highly purified VIII:C which had been prepared by the process of U.S. Pat. No. 4,361,509.

Mice were injected with highly purified factor VIII:C according to the following procedure. On day zero, the mice were injected intraperitoneally with a composition prepared by dissolving (or suspending) 10 ug of the protein in 0.1 ml of buffer containing 0.05M Tris, 0.15M sodium chloride, 0.02% sodium azide, 1 mM phenyl methyl sulfonyl fluoride, trasylol 10 units/ml at pH 7.3, and shaking with an equal volume of complete Freund's adjuvant. On day 14, the mice were again injected with the same material except that incomplete Freund's adjuvant was substituted for complete Freund's adjuvant. On day 21, the injection of day 14 was repeated. On day 38, the mice were injected with purified VIII:C only. On day 42, the spleens of the mice were removed and fused according to a standard procedure, of the type described by J. P. Brown et al "Protein Antigens of Normal and Malignant Human Cells Identified by Immunoprocipitation with Monoclonal Antibodies", JOURNAL OF BIOLOGICAL CHEMISTRY, Vol. 225, pp. 4980–4983 (1980). The standard technique was varied only to the extent that 35% polyethylene glycol 1000 was substituted for 50% polyethylene glycol.

The antibodies were selected using the assay procedure described above in Example I, in the paragraph with the heading "Production of monoclonal antibody against VIII:C", except that antibodies which did not neutralize VIII:C activity were also subcloned and treated as described below.

The clones which were positive were subcloned twice and stable clones producing antibody to VIII:C were then injected into the peritoneal cavities of Balb/C mice which had been pretreated intraperitoneally with 0.5 ml of pristane at least four days prior to injection of cells. Hybridoma cells were injected at concentrations of approximately $5 \times 10^6$ cells per mouse in 0.5 ml of Dulbecco's modified Eagle's medium without fetal bovine serum. The mice were tapped when bloated and ascites fluid was collected in heparin at approximately 10 units/ml. Ascites fluid from multiple mice was pooled to provide a convenient volume for subsequent isolation of the monoclonal IgG. The antibodies were precipitated from ascites fluid using 50% ammonium sulfate, and then reprecipitated two more times. The anti-VIII:C antibodies so raised corresponding to (B), (C) and (D) above were bound to agarose beads and shown to bind purified VIII:C from solution.

Separate batched of VIII:C, one untreated and one subjected to thrombin proteolysis, were then analyzed by the SDS-PAGE steps described in Example 1. Then, each band was transferred electrophoretically (Western transfers) from the gel onto a nitrocellulose sheet. The apparatus used was Bio-Rad "Trans-Blot" cell, and Bio-Rad Model 160.1.6 power supply (Bio-Rad Laboratories, Richmond, Calif.). The transfer buffer was 25 mM Tris with glycine added to pH 8.3, 20% methanol. Transfers were carried out over 16-24 hours at 90 volts and 100 milliamperes.

The specific polypeptides with which each of the antibodies reacted were determined using a procedure adapted from W. M. Burnette, "Western Blotting: Electrophoretic Transfer of Proteins from Sodium Dodecyl Sulfate Polyacrylamide Gels to Unmodified Nitrocellulose and Radiographic Detection with Antibodies and Radioiodinated Protein A", Analytical Biochemistry, Vol. 112, pp. 195-203 (1981).

"Buffer D:" was 10 mM Tris chloride, 0.15M NaCl, 0.02% sodium azide, pH 7.4. All reactions were carried out at room temperature.

1. Place the nitrocellulose sheet with the transferred protein in a tray containing 100 ml of Buffer D and 0.25% gelatin. Place the tray on a rotary shaker and shake slowly for 30 minutes.
2. Then add the monoclonal antibody to the tray (either 0.1%-1% of ascites fluid or 1 mg of purified IgG). Shake for 120 minutes.
3. Wash the nitrocellulose sheet as follows:
   (a) 10 minutes with 100 ml of Buffer D
   (b) 30 minutes with 100 ml of Buffer D and 0.05% of Nonidet-P-40, with changes at 10 and 20 minutes.
   (c) 10 minutes with 100 ml of Buffer D.
4. Soak the nitrocellulose sheet in Buffer D plus 0.25% gelatin and $I^{125}$-labelled purified rabbit anti-mouse IgG for 30 minutes.
5. Wash the nitrocellulose sheet as follows:
   (a) 10 minutes with 100 ml of Buffer D.
   (b) 16-24 hours with 100 ml of Buffer D plus 0.1% Nonidet P-40 and 0.5M NaCl.
   (c) 10 minutes with 100 ml of Buffer D.
6. Blot the nitrocellulose sheet between two sheets of filter paper and then store the nitrocellulose sheet in a sealed plastic bag.
7. To determine which antibodies and polypeptides had reacted,
   (a) Prepare an autoradiograph of the nitrocellulose sheet, using standard procedures known in the literature.
   (b) Compare the autoradiograph with a nitrocellulose sheet onto which VIII:C was transferred but which had been stained with Coomassie blue R250 rather than reacted with monoclonal antibody.

These steps demonstrated that the following distinct antibodies had been raised.

Four antibodies reacted with the polypeptide of $M_r=92,000$, the $M_r=108,000$ and larger polypeptides, one or the other of the polypeptides of $M_r=54,000$ or 44,000 present in terminal thrombin digests, and no other polypeptides. This demonstrates the origin of these two latter polypeptides from the polypeptide of $M_r=92,000$ as the result of thrombin cleavage. It also shows that two epitopes on the $M_r=92,000$ polypeptide survive that cleavage, and that these epitopes are not present on the $M_r=79,000-80,000$ doublet.

A fifth antibody reacted with the doublet of $M_r=79,000-80,000$, and with polypeptides of $M_r=108,000$ and greater, but not with the polypeptide of $M_r=92,000$ nor with any of the polypeptides present in terminal thrombin digests. This demonstrates that the $M_r=79,000-80,000$ doublet possesses an epitope which is not present on the $M_r=92,000$ polypeptide; and that the epitope is destroyed by thrombin digestion of the $M_r=79,000-80,000$ doublet.

The reaction profiles of these five antibodies indicate that the $M_r=92,000$ and $M_r=79,000-80,000$ polypeptides derive from a common precursor or precursors.

A sixth antibody reacted only with polypeptides of $M_r=108,000$ and greater. Since it did not react with any polypeptides present in terminal thrombin digests, the epitope with which it reacted is destroyed by thrombin digestion.

To prepare and store a biological preparation of one or more of these antibodies, the corresponding monoclonal IgG may be isolated from heparinized pooled ascites fluid immediately after collection or a frozen portion of the stored solution may be thawed. Regardless of whether fresh or frozen material is used, the solution is brought to 4° C. and treated with an equal volume of phosphate buffered saline solution (PBS) (PBS: 1.6 g sodium phosphate, monobasic monohydrate; 8.4 g sodium phosphate, dibasic anhydrous; 61.4 g sodium chloride; water to 7 liters; pH=7.2). The diluted ascites is precipitated by dropwise addition with stirring at 4° C. Centrifugations are preferably carried out at 14,000 rpm for 60 minutes (30,000×g). The supernatant solution of ascites is precipitated twice more with SAS and the mixture of precipitate and supernatant liquid stirred and centrifuged in the same manner as in the first cycle. The pellets resulting from the third precipitation are resuspended in a volume of PBS equal to that of the diluted ascites fluid and then dialyzed exhaustively against PBS. Clots appearing in the dialysis bags are removed by centrifugation at 20° C. The dialyzed IgG is adsorbed by stirring it with a 5% aqueous solution of aluminum hydroxide at room temperature and centrifuging at 20° C. after adsorption. The adsorption treatment is repeated at least three more times using 2.5% aluminum hydroxide solution for each treatment after the first. The adsorbed IgG is brought to 4° C. and reprecipitated once with SAS as described above. The precipitated pellets may be stored at −20° C. until used.

Two preferred procedures for purifying the monoclonal antibodies and maintaining biological preparations containing them are described in P. L. Ey et al., "Isolation of Pure $IgG_1$, $IgG_{2a}$, and $IgG_{2b}$ Immunoglobulins from Mouse Serum Using Protein A-Sepharose." Immunochemistry, Vol. 15, pp. 429-436; and in C. Bruck et al., "One-Step Purification of Mouse Monoclonal Antibodies from Ascitic Fluid by DEAE Affi-Gel Blue Chromatography." J. Immunological Methods, Vol. 53, pp. 313-319 (1982).

What is claimed is:

1. A biological preparation made by a process comprising the steps of:
   (a) digesting human factor VIII:C in a digestion mixture with an effective amount of a protease under digestion conditions to form a Factor VIII:C coagulant polypeptide complex in association with one or more polypeptides; and wherein said complex is characterized in that:
      (i) the complex consists essentially of more than one polypeptide which exhibits bands at points corresponding to $M_r$ values of about 92,000, about 80,000, and about 79,000; or of about 92,000, about 72,000, and about 71,000; or of about 92,000, about 80,000, about 79,000, about 72,000, and about 71,000; when subjected to sodium dodecyl sulfatepolyacrylamide gel electrophoresis;

(ii) the complex exhibits specific coagulant activity higher than 1800 Units/mg over a continuous period of at least about 10 minutes; and (iii) the complex binds to an antibody for human Factor VIII:C;

(b) discontinuing the digestion while said polypeptide complex is still present in said digestion mixture.

2. A biological preparation made by a process comprising the steps of:

(a) digesting human factor VIII:C in a digestion mixture with an effective amount of a protease under digestion conditions to form a Factor VIII:C coagulant polypeptide complex in association with one or more polypeptides; and wherein said complex is characterized in that:

(i) the complex consists essentially of more than one polypeptide which exhibits bands at points corresponding to $M_r$ values of about 92,000, about 80,000, and about 79,000; or of about 92,000, about 72,000, and about 71,000; or of about 92,000, about 80,000, about 79,000, about 72,000, and about 71,000; when subjected to sodium dodecyl sulfatepolyacrylamide gel electrophoresis;

(ii) the complex exhibits specific coagulant activity higher than 1800 Units/mg over a continuous period of at least about 10 minutes; and (iii) the complex binds to an antibody for human Factor VIII:C;

(b) discontinuing the digestion while said polypeptide complex is still present in said digestion mixture;

(c) concentrating the digestion mixture so that said complex comprises at least about 1% by weight of the proteinaceous matter in the concentrated mixture.

3. A biological preparation made by a process comprising the steps of:

(a) digesting human factor VIII:C in a digestion mixture with an effective amount of a protease under digestion conditions to form a Factor VIII:C coagulant polypeptide complex in association with one or more polypeptides; and wherein said complex is characterized in that:

(i) the complex consists essentially of more than one polypeptide which exhibits bands at points corresponding to $M_r$ values of about 92,000, about 80,000, and about 79,000; or of about 92,000, about 72,000, and about 71,000; or of about 92,000, about 80,000, about 79,000, about 72,000, and about 71,000; when subjected to sodium dodecyl sulfatepolyacrylamide gel electrophoresis;

(ii) the complex exhibits specific coagulant activity higher than 1800 Units/mg over a continuous period of at least about 10 minutes; and (iii) the complex binds to an antibody for human Factor VIII:C;

(b) discontinuing the digestion while said polypeptide complex is still present in said digestion mixture;

(c) concentrating the digestion mixture so that said complex comprises at least about 60% by weight of the proteinaceous matter in the concentrated mixture.

4. A biological preparation made by the process of claim 1 wherein the human factor VIII:C has previously been purified.

5. A biological preparation made by the process of claim 2 wherein the human factor VIII:C has previously been purified.

6. The biological preparation of claim 1 having over 1800 Units/mg of factor VIII:C coagulant activity, which activity is due to the presence in the preparation of said polypeptide complex.

7. The biological preparation of claim 2 having over 1800 Units/mg of factor VIII:C coagulant activity, which activity is due to the presence in the preparation of said polypeptide complex.

8. The biological preparation of claim 3 having over 1800 Units/mg of factor VIII:C coagulant activity, which activity is due to the presence in the preparation of said polypeptide complex.

9. The biological preparation of claim 4 having over 1800 Units/mg of factor VIII:C coagulant activity, which activity is due to the presence in the preparation of said polypeptide complex.

10. The biological preparation of claim 5 having over 1800 Units/mg of factor VIII:C coagulant activity, which activity is due to the presence in the preparation of said polypeptide complex.

* * * * *

UNITED STATES PATENT AND TRADEMARK OFFICE
CERTIFICATE OF CORRECTION

PATENT NO. : 5,101,016
DATED : March 31, 1992
INVENTOR(S) : Zimmerman et al.

It is certified that error appears in the above-identified patent and that said Letters Patent is hereby corrected as shown below:

Column 1, line 12, insert the following: --This invention was made with government support under Grant Number HL 15491 awarded by The National Institute of Health. The government has certain rights to this invention.--

Signed and Sealed this

Twenty-second Day of February, 1994

Attest:

BRUCE LEHMAN

Attesting Officer          Commissioner of Patents and Trademarks